(12) United States Patent
Blum et al.

(10) Patent No.: US 6,194,203 B1
(45) Date of Patent: *Feb. 27, 2001

(54) IMMORTALIZED ADULT HUMAN COLON EPITHELIAL CELL LINE

(75) Inventors: Stéphanie Blum, Lausanne; Andrea Pfeifer, St-Legier; Yvonne Tromvoukis, Effretikon, all of (CH)

(73) Assignee: Nestec S.A., Vevey (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/839,271

(22) Filed: Apr. 17, 1997

(30) Foreign Application Priority Data

Apr. 19, 1996 (EP) .................................................. 96201064

(51) Int. Cl.$^7$ ...................................................... C12N 5/08
(52) U.S. Cl. .......................................... 435/371; 435/366
(58) Field of Search ...................................... 435/371, 366

(56) References Cited

U.S. PATENT DOCUMENTS

| | | | | |
|---|---|---|---|---|
| 4,885,238 | * | 12/1989 | Reddel et al. | 435/29 |
| 5,376,542 | | 12/1994 | Schlegal | 435/172.2 |
| 5,462,870 | * | 10/1995 | Chopra | 435/240.2 |
| 5,529,920 | * | 6/1996 | Cole et al. | 435/240.2 |
| 5,610,043 | * | 3/1997 | Webber et al. | 435/172.3 |
| 5,672,498 | * | 9/1997 | Walker et al. | 435/240.2 |

FOREIGN PATENT DOCUMENTS

| | | |
|---|---|---|
| 37 11 699 A1 | 11/1988 | (DE) . |
| 577 904 | 1/1994 | (EP) . |
| WO 89/05862 | 6/1989 | (WO) . |

OTHER PUBLICATIONS

American Type Culture Collection, 1988, *Catalogue of Cell lines & Hybridomas*, 6th Ed. pp. 146, 174, and 344.
Baten et al., 1992, *FASEB J.*6:2726–2734.
Bernet et al., 1993, *Applied Env. Micro.* 59:4121–4128.
Bernet et al., 1994, *Gut* 35:483–489.
Berry et al., 1988, *Br. J. Cancer* 57:287–289.
Bettger et al., 1981, *PNAS USA* 78:5588–5592.
Donehower et al., 1992, *Nature* 356:215–221.
J. Fogh, ed., 1975, *Human Tumour Cells In Vitro* pp. 145–159.
Fogh et al., 1977, *J. Natl. Cancer Inst.* 58:209–214.
R.I. Freshney, 1987, *Culture of Animal Cells, A Manual of Basic Technique* pp. 74–84.
Gibson et al., 1991, *Gut* 35:791–797.
Hargest & Williamson, 1995, *Gut* 37:826–829.
Kulkarni et al., 1995, *Carcinogenesis* 16:2515–2521.
Lavigeur et al., 1989, *Mol. Cell. Biol.* 9:3982–3991.
Moyer & Aust, 1967, *In Vitro Cell. & Dev. Biol.* 23:141–146.
Moyer & Aust, 1984, *Science* 224:1445–1447.
Pfeifer et al., 1993, *PNAS USA* 90:5123–5127.
Sahi et al., 1995, *Gastroenterol.* 108:A321.
Sanderson & Walker, 1995, *Int. Arch. Allergy Immunol.* 107:396–397.
Stauffer et al., 1995, *Am. J. of Surgery* 169:190–196.
Derwent Acc No. 88–324194/46.
Derwent Acc No. 94–009846/02.
Paraskeva et al., 1990, Anticancer Research 10:1189–1200.*
Moyer M. T. and Poste G.H. Colon Cancer Cells. Academic Press, Inc., San Diego, California, 1990. p. 85,202.*
Rak et al. "Massive programmed cell death in intestinal epithelial cells in duced by three–dimensional growth conditions:suppression by mutantc–h–ras oncogene expression", Journal of Cell Biology, 1995, vol. 131, No. 6, part 1, pp. 1587–1598.*
ATCC Cell Llnes and Hybridomas Catalogue. 8th edition. 1994. pp. 173, 174, 516, 517, 543.*

* cited by examiner

*Primary Examiner*—Sandra E. Saucier
*Assistant Examiner*—Vera Afremova
(74) *Attorney, Agent, or Firm*—Pennie & Edmonds LLP (57) ABSTRACT

Immortalized adult human colon epithelial cell line, which does not express tumour markers, which expresses metabolic markers specific for the non-immortalized human epithelial cells and metabolic differentiation markers specific for the non-immortalized epithelial cells of the human colon, and which is capable of adhering in vitro to the strain of lactic acid bacterium CNCM-1225. Serum-free culture medium characterized in that it comprises trace elements, vitamins consisting of vitamin C and retinoic acid, and hormones consisting of triiodothyronine, dexamethasone, hydrocortisone, bovine pituary gland extract, insulin, EGF and transferrin. Process for the immortalization of epithelial cells of the human colon, in which a culture of primary epithelial cells derived from the human colon is prepared, the culture is infected with a recombinant virus, the immortalized cells are cultured in the serum-free culture medium according to the invention. Process for identifying the mutagenic, toxic or beneficial effect of an agent on the metabolism of the cells of the intestinal tract, in which (1) an agent suspected of being a mutagenic, toxic or beneficial agent for the metabolism of the cells of the intestinal tract is reacted, cultured or brought into contact with a culture comprising a cell line according to the invention, and (2) the effects of the said agent on the said cell line are determined or measured. Use of the cells according to the invention as an active pharmaceutical agent. In particularly, cell line DSM ACC2258.

14 Claims, 2 Drawing Sheets

IMMORTALIZED ADULT HUMAN COLON EPITHELIAL CELL LINE

FIELD OF THE INVENTION

The subject of the present invention is a new human epithelial colon immortalized cell line, a method for obtaining this line, as well as any use of this line, especially in processes for the identification of mutagenic, toxic or beneficial agents for the metabolism of the cells of the intestinal tract.

BACKGROUND

For many years, efforts have been made to develop human cell lines adapted to the study of human diseases, such as infections, inflammations or cancers, for example. Among the cells often involved in the onset of diseases, there are the epithelial cells, in particular the epithelial cells of the intestinal tract which are sensitive to the surroundings of the human body, and especially to the conditions of its diet.

The epithelial cells differ from other cells of the human body in the expression of compounds or structures which are mainly found in the epithelial cells, such as for example cytokeratins (Moll et al., Cell, 31, 11–24, 1982), connections between the cells (Gumbiner et al., Cell, 69, 385–387, 1992), alkaline phosphatase which is specific to the intestine (Dudeja et al., Gastroenterology, 105, 357–366, 1993), cytochromes P450 (Mercurio et al., Biochem. Biophy. Research Communications, 210, No. 2, 350–355, 1995; McKinnon et al., Gut, 36, 259–267, 1995), enzymes involved in cellular oxidation defense (Cu/Zn-superoxide dismutase, glutathione peroxidase and catalase; Albers et al., Toxicology and Applied Pharmacology, 109, 507–513, 1991) and/or in the detoxification of electrophiles (glutathione-S-transferase and quinone reductase; Chenevix- Trench et al., Carcinogenesis, 16, No. 7, 1655–1657, 1995), and vimentin (Richard et al., Arch. Dematol. Res., 282, 512–515, 1990), In addition, the epithelial cells of the human intestinal tract are capable of adhering lactic acid bacteria in vitro (Bernet et al., Gut, 35, 483–489, 1994; U.S. Pat. No. 5,032,399)

Finally, the epithelial cells of the human colon also differ from other human epithelial cells in the expression of compounds or structures found mainly in the epithelial cells of the human intestine, such as, for example, surface villosities (Friedrich et al., Bioassays, 12, No. 9, 403–408, 1990), sucrose isomaltase (Gibson et al., Gut, 35, 791–797, 1994; Paul et al., Am. Pysiol. Soc., C266-C278, 1993), certain class II major histocompatibility antigens (Mayer et al., Gastroenterology, 100, 3–12, 1991), and dipeptidylpeptidase IV (DPPIV; Hauri et al., J. Cell. Biol., 101, 836–851, 1985).

The preparation of an epithelial cell line of the human colon may be carried out by the selection of human cancer cells. Stauffer et al. thus describe the selection of two lines NCM356 and NCM425 which comprise the p53 mutation and which express in particular the tumour antigen CEA (The American journal of surgery, 169, 190–196, 1995). These cells represents a tumorigenic transformation stage, and are of interest for studying the development of the tumorigenic transformation of the epithelial, cells.

Other human colon epithelial cell lines isolated from a human colon adenoma are also known, such as, for example, the lines CaCO-2 (ATCC HTB37; Fogh et al., J. Natl. Cancer Inst., 58, 209–214, 1977) and HT29 (ATCC HTB38; Fogh et al., Human tumour Cells In Vitro, 145–159, 1975)

It is also possible to immortalize normal cells, that is to say make them capable of multiplying indefinitely. Indeed, normal cells do not survive more than a ten passages. For that, techniques for the transfection of cells, with the aid of specially adapted vectors, such as the SV40 vector comprising a sequence of the large T antigen (R. D. Berry et al., Br. J. Cancer, 57, 287–289, 1988), or a vector comprising DNA sequences of the human papillomavirus (U.S. Pat. No. 5,376,542), are generally used.

Sanderson et al. have thus immortalized normal cells of the foetal small intestine (Int. Arch. Allergy Immunol., 107, 396–397, 1995). However, these cells still remain physiologically distant from normal adult cells.

Up until now, no immortalization of normal epithelial cells of the adult human colon has been reported. Even if the immortalization techniques are known, it is still quite difficult to find the optimum conditions for immortalizing a human cell so that it conserves its original characteristics, and without exhibiting signs of a tumorigenic transformation.

One of the conditions to propagate immortalized cells is their growth in a particular culture medium. The culture media described in the literature are each specific for a cell type and cannot be easily applied to other cell types. By way of example, there may be mentioned the serum-free media described by Gibson et al. (Gut, 35, 791–797, 1991), Pfeifer et al. (Proc. Natl. Acad. Sci. USA, 90, 5123–5127, 1993) and Kulkani et al. (Carcinogenesis, 16, No. 10, 2515–2521, 1995).

The aim of the invention is to provide new human colon epithelial cell lines which are genetically and physiologically related to the normal epithelial cells of the human colon, to the extent that it is difficult to differentiate them. In particular, these lines do not express tumour markers. These lines express, in addition, numerous specific markers found in normal epithelial cells of the human colon.

SUMMARY OF THE INVENTION

To this end, the invention relates to any immortalized human colon epithelial cell lines, which does not express tumour markers, which expresses metabolic markers specific for the non-immortalized human epithelial cells and metabolic differentiation markers specific for the non-immortalized epithelial cells of the human colon, and which is capable of adhering in vitro the CNCM-1225 strain of lactic acid bacterium.

The subject of the invention is also a serum-free culture media adapted to the culture and immortalization of epithelial cells of the human colon. This medium comprises the constituents usually found in the serum-free media used to culture animal cells, such as, for example, inorganic salts, glucose, sodium pyruvate, amino acids, bovine serum albumin (BSA), amines such as phosphoethanolamine and ethanolamine, vitamins, and hormones. This medium comprises, in addition, a new combination of some of its constituents, namely trace elements, vitamins consisting of vitamin C and retinoic acid, hormones consisting of triiodothyronine, dexamethasone, hydrocortisone, extract of bovine pituarity gland, insulin, epithelial growth factor (EGF) and transferrin.

Another aspect of the invention relates to a new process for the immortalization of epithelial cells of the human colon, in which a culture of primary epithelial cells derived from the human colon is prepared, the culture is infected with a recombinant virus, and the immortalized cells are cultured in the serum-free culture medium described above.

Another aspect of the invention relates to a process for identifying the mutagenic, toxic or beneficial effect of an agent on the metabolism of the cells of the intestinal tract, in which (1) an agent suspected of being a mutagenic, toxic or beneficial agent for the metabolism of the cells of the intestinal tract is reacted, cultured or brought into contact with a culture comprising a cell line described above, and (2) the effects of the said agent on the said cell line are determined or measured.

The invention also relates to a diagnostic kit comprising the immortalized epithelial cells of the human colon described above, the culture medium described above, and the reagents for determining a metabolic response of the said cells to mutagenic, toxic or beneficial agents.

Finally, the subject of the invention is also any uses of the cell lines described above, in processes for the identification of mutagenic, toxic or beneficial agents for the metabolism of the cells of the intestinal tract, as well as any uses of the said lines as an active pharmaceutical agent.

DETAILED DESCRIPTION OF THE INVENTION

Within the framework of the present invention, the expressions "normal cells", "primary cells" or "non-immortalized cells" designate epithelial cells of the human colon which can be collected from the colon of a healthy adult not having crippling physiological or genetic deficiencies, and which can be cultured for a limited time without losing their original differentiation characteristics.

On the other hand, the expression "immortalized cells" designates cells which have undergone a genetic manipulation, by means of a DNA construct, which makes them capable of multiplying indefinitely, that is to say at more than 60 passages. The cancer cells selected by Stauffer et al., or the lines CaCO-2 and HT29 are thus not considered as cells which have been immortalized according to the present invention.

Likewise, the word "passage" designates the process consisting in taking an aliquot of a confluent culture of a cell line, in inoculating into fresh medium, and in culturing the line until confluence or saturation is obtained. The cell lines are thus traditionally cultured by successive passages in fresh media. It should be noted that the cell lines may loose their original differentiation characteristics after several successive passages. It is therefore extremely advantageous to be able to have a line whose characteristics are conserved even after numerous passages, preferably at least 60 passages.

Finally, the expression "original differentiation characteristics" designates both the markers found specifically on the human epithelial cells and the differentiation markers found specifically on the human colon epithelial cells.

The immortalized human colon epithelial cell lines according to the invention do not express tumour markers, that is to say do not have carcinogenic mutations or do not express messenger RNAs (mRNAs), or differentiated cellular structure and/or proteins characteristic of the transformation of the cells into tumour cells. The presence of these markers may be detected by hybridization or RT-PCR of MRNA with specific radiolabeled probes, for example. The presence of a marker in a cell does not mean that the said cell is capable of conferring a cancer, after a few months, on a mouse without immune defence, but rather reflects a tumorigenic transformed state of the cells compared with the original cells from which they are derived.

Preferably, the line according to the present invention does not have the p53 mutation (Lavigeur et al., Mol. Cell. Biol., 9, 3982–3991, 1989; Donehower et al., Nature, 356, 215–221, 1992), the carcinoma embryonic antigen (CEA; Stauffer et al.), and/or mutation in the APC gene (adenomatous polyposis coli; Hargest et al., Gut,37, 826–829, 1995).

The epithelial cell lines according to the invention express, on the other hand, metabolic markers specific for normal human epithelial cells. These markers may be a messenger RNA (mRNA), a protein, and/or a differentiated cellular structure, which is generally found only in the majority of the human epithelial cells, capable of being derived from the skin, the eye, the intestinal tract, or the liver, for example. The human epithelial cells according to the invention may therefore express at least two markers found in different types of epithelial cells. Preferably, the cells according to the invention express the said markers chosen from the group formed by at least cytokeratins, connections between the cells (also called "tight junctions"), intestine alkaline phosphatase, cytochromes P450, glutathione-S-transferase (GST), quinone reductase (QR), Cu/Zn-superoxide dismutase (SOD), glutathione peroxidase (GP) and catalase (CA).

The lines according to the invention may therefore express enzymes involved in cellular oxidation (SOD, GP and CA) and/or the detoxification of electrophiles (GST and QR). These lines are therefore particularly adapted to the study of the phenomena of inflammations or irritations of the mucous membranes of the human colon.

The cell lines according to the invention also express metabolic differentiation markers which are specific for the non-immortalized epithelial cells of the human colon. These markers may be an mRNA, a protein, or a differentiated cellular structure which is found only in the epithelial cells of the colon. Preferably, the lines according to the invention express, as metabolic differentiation marker, at least two markers chosen from the group formed by surface villosities, sucrose isomaltase, class II major histocompatibility complexes which are specific to colon epithelial cells, and dipeptidylpeptidase IV.

Likewise, the lines according to the invention preferably express the HLA-DR and HLA-DP antigens of the class II major histocompatibility complexes (MHC II), and do not express the HLA-DQ antigen, in the presence of human gamma-interferon (expression of HLA-DQ has been associated with tumorigenicity).

The lines according to the invention should also be capable of adhering in vitro the Lactobacillus johnsonii strain CNCM-I-1225. For that, a culture of lactic acid bacterium simply has to be spread over a confluent culture of a line according to the invention, the confluent culture washed and then the number of bacteria adhering to the villosities of the said lines measured. Preferably, a line according to the invention is capable of adhering in vitro the strain of lactic acid bacterium CNCM-I-1225 at the rate of at least 80 bacteria per 100 colon cells according to the invention, especially 80–200.

The lines according to the invention should also be capable of adhering in vitro to *Clostridium difficile* and/or to other adherent lactic bacteria, like bifidobacteria, in particulare the bifidobacteria described in Applied Env. Microb., 59, 4121–4128, 1993 and in EP577904 (Nestle), which have been deposited at the Pasteur Institut, Paris, France, where they received the deposit numbers CNCM I-1226, CNCM I-1227 and CNCM I-1228, respectively.

The lines according to the invention should also be capable of expressing many cytokines, after being in contact with an inflammation agent, notably cytokines IL-1β, IL-1Ra, TNFα, IL-6 and IL-8, for instance.

The invention also relates in particular to an immortalized line according to the invention which has been deposited at the Deutsche Sammlung Von Mikroorganismen und Zellkulturen, Mascheroder Weg 1b, D-38124 Braunschweig, Germany, on Apr. 16, 1996, where it received the deposit number DSM ACC2258.

The human colon epithelial lines according to the invention advantageously conserve their original differentiation characteristics even after numerous passages, especially at least 40–80 passages. There may be noted however, after the 40th passage, or even before, a change in the karyotype of the lines following the loss of fragments of chromosomes. However, these lines generally conserve as for even the same intact set of each pair of chromosomes, which allows them to also conserve the expression of their original differentiation characteristics.

Another aspect of the present invention relates to a serum-free culture medium adapted to the culture and to the immortalization of epithelial cells of the human colon according to the invention. This culture medium is particularly adapted to maintain indefinitely, during successive passages, the original differentiation characteristics of the lines according to the invention. If other culture media are used, the lines according to the invention could thus loose their original differentiation characteristics following a few successive passages, for example 5–10 passages. This medium is also essential for successfully immortalizing lines according to the invention. The suppression of one of its characteristic constituents thus generally leads to the failure of the immortalization of epithelial cells of the colon according to the invention.

This medium may comprise all the constituents usually found in serum-free animal cell culture media, namely inorganic salts, glucose, a buffer (HEPES, for example: Biofluids), sodium pyruvate, amino acids, BSA, phosphorlyethanorlamine, ethanolamine, vitamins, and hormones, for example. Commercial culture media, such as the DMEM medium (Biofluids Inc., USA) may thus serve as base for the preparation of this medium.

The novelty of the medium according to the invention lies in a new combination of some of its constituents, whereas the other compounds usually necessary may vary within the limits known to persons skilled in the art. These essential constituents are trace elements, vitamins consisting of vitamin C and retinoic acid, and hormones consisting of triiodothyronine, dexamethasone, hydrocortisone, bovine pituary gland extract, insulin, EGF and transferrin.

This culture medium may thus comprise 1–100 nM trace elements, 10–1000 nM retinoic acid, 10–1000 nM triiodothyronine (T3), 0.1–50 nM dexamethasone, 1–100 nM hydrocortisone, 1–100 µg/ml of vitamin C, 1–100 µg/ml of bovine pituary gland extract, 0.1–50 µg/ml of insulin, 0.1–50 ng/ml of EGF and 0.1–100 µg/ml of transferrin.

Among the trace elements, there may be chosen the compounds chosen from the group formed by selenium, manganese, silicate, molybdenum, vanadium, nickel, tin, and their salts, for example.

Among the inorganic salts usually included in the medium, there may be chosen salts form the group formed by sodium chloride, potassium chloride, potassium sulphate, calcium chloride, dibasic sodium phosphate, sodium bicarbonate, ferric nitrite, ammonium metevanadate, ammonium molybdate, cupric sulphate, magnesium chloride, manganese chloride, nickel sulphate, sodium acetate, sodium pyruvate, sodium selenite, sodium silicate, tin chloride, and zinc sulphate, for example.

In particular, care may be taken so that the medium contains less than 80 µM of calcium in the form of inorganic salts, so as to inhibit the development of contaminating fibroblasts. However, calcium concentration can be raised to 1 mM, which was necessary for some experiments (polarisation, expression of thigh junction proteins, etc.). After several passages, there is no further risk to propagate fibroblasts, which might be early contaminants due to the processing of primary cells.

Likewise, among the other vitamins usually included in the medium, there may be chosen other vitamins chosen from the group formed by calcium D-pantothenate, choline chloride, folic acid, inositol, nicotinamide, pyridoxine, riboflavin, thiamine, biotin and cyanocobalamin, for example.

Finally, a culture medium which makes it possible to successfully obtain lines according to the invention preferably has the composition B50 defined in Table 1 below.

Another aspect of the invention relates to a process for the immortalization of epithelial cells of the human colon, in which a culture of primary epithelial cells derived from the human colon is prepared, the culture is infected with a recombinant virus, the immortalized cells are cultured in the serum-free culture medium described above.

Before that, the following steps are preferably used:
(1) a sample of epithelial tissues of a human colon is obtained;
(2) this sample is prepared for the purpose of its culture in vitro;
(3) the epithelial cells are inoculated into a serum-free culture medium and on culture plates comprising a coating which facilitates the attachment of the cells and their growth;
(4) the medium is changed as many times as necessary in order to optimize the confluent growth;
(5) the cells are infected with a recombinant virus;
(6) and the immortalized cells are cultured in the serum-free culture medium described above.

In greater detail, stage 1) relates to the obtaining of samples of colon cells from normal individuals during surgical acts on the intestinal tract. In stage 2), the sample may be washed in the culture medium, cut into pieces, and the epithelial part separated from other tissues by physical and/or chemical means. For example, the pieces of tissue may be placed in a solution comprising about 0.5% trypsin and 0.1% EDTA for a time sufficient to achieve separation of the cells, and then a trypsin inhibitor added for a few minutes, and finally culture medium, preferably that described above, is added.

In stage 3), the epithelial cells may be inoculated on plates in a serum-free culture medium, preferably that described above. The culture plates preferably have a coating consisting of a solution of fibronectin, BSA and type 1 collagen (see Lechner et al., J. Tissue Cult. Meth., 9, 43–48,1985).

In stage 4), the culture medium containing the epithelial cells is changed as many times as necessary so as to optimize a confluent growth. Preferably, the medium is replaced every two days. After having reached a confluence of the order of 90% of the available surface area, which generally occurs 10 days after the inoculation, the cells are separated by treatments in solutions of trypsin and EDTA.

The separated cells are transferred in stage 5) into an infection medium, for example that described above, on culture plates preferably having the coating described above. The cells are then infected in a conventional manner with a recombinant virus. Numerous transfection techniques are available to persons skilled in the art. By way of example, there may be mentioned the techniques described in WO96/07750, by Claudia Chen et al. (Mol. and Cell. Biol., 7, 2745–2752, 1987) or by Wilson et al. (Analytical Biochemistry, 226, 212–220, 1995).

Preferably, a recombinant SV40 virus comprising the T Antigen (T-Ag), an inactivated virus replication origin (MuLV retrovirus), and a selectable gene are used. By way of example, the construct presented in FIG. 1, whose sequence is available in the GeneBank data bank (accession No. M64753; Stockshlaeder et al., Human Gen. Therapy, 2, 33–39, 1991), may thus be used. Other appropriate vectors may also be easily constructed by persons skilled in the art from commercially available vectors comprising, for example, the gene encoding T-Ag, a selectable gene and/or a human replication origin. By way of example, there may be mentioned the plasmids ATCC37460 and ATCC37640 which contain the gene encoding T-Ag.

In stage 6), the epithelial cells are transferred into a fresh growth medium, on culture plates preferably comprising the coating described above.

Knowing the new and original properties of the epithelial cell lines according to the invention, their application may be envisaged in immunological, pharmacological and toxicological studies The lines according to the invention are thus particularly adapted for screening mutagenic, toxic or beneficial agents for the metabolism of the cells of the intestinal tract, for example in a process in which (1) an agent suspected of being a mutagenic, toxic or beneficial agent for the metabolism of the cells of the intestinal tract is reacted, cultured or brought into contact with a culture comprising a cell line according to the invention, and (2) the effects of the said agent on the said cell line are determined or measured by monitoring the expression of known markers of mutagenic, toxic, or beneficial responses. For example, a toxic response such as inflamation may be monitored by measuring the level of cytokines produced by the culture after exposure to the agent (see Example 1, section 8).

It may therefore also be envisaged to prepare a diagnostic kit comprising the epithelial cells according to the invention, the culture medium according to the invention, and reagents for determining a metabolic response of the said cells to mutagenic, toxic or beneficial agents.

The lines according to the invention are also adapted to the expression of recombinant proteins. The methods of transfection of foreign DNA are now well known to persons skilled in the art (see for example WO94/05472)

The lines according to the invention also have a potential usefulness in gene therapy ex vivo. These lines might indeed constitute a suitable tool for developing recombinant cells expressing genes of interest for the purpose of a therapeutic application. One advantage additionally presented by the lines according to the invention is that they are not exposed to an animal serum, which considerably reduces the risks of potential contaminations by viruses or other pathogenic agents.

The present invention is described in greater detail below with the aid of the additional description which follows, which refers to examples of preparations of cell lines according to the invention. These examples are preceded by a description of the culture media used, as well as a comparative example. It goes without saying, however, that these examples are given by way of illustration of the subject of the invention and do not in any way constitute a limitation thereto. The cell line culture, the preparation of SV40 vectors, the transfection and the analysis of the expressions of the markers are, unless otherwise stated, carried out according to the procedures described in the manual by Sambrook et al. (Molecular Cloning, A Laboratory Manual, Cold Spring Harbor Laboratory Press, U.S.A., 1989). The percentages are given by weight, unless otherwise indicated.

TABLE 1

Culture media:

| Constituents | Medium A50 | Medium B50 |
|---|---|---|
| INORGANIC SALTS | | |
| NaCl | 6.400 g/l | 6.400 g/l |
| KCl | 0.400 g/l | 0.400 g/l |
| $MgSO_4 \cdot 7H_2O$ | 0.200 g/l | 0.200 g/l |
| $CaCl_2$ | 0.200 g/l | 0.200 g/l |
| $NaH_2PO_4 \cdot H_2O$ | 0.13 g/l | 0.13 g/l |
| $NaHCO_3$ | 3.7 g/l | 3.7 g/l |
| $Fe(NO_3)_2 \cdot 9H_2O$ | 0.0001 g/l | 0.0001 g/l |
| OTHER COMPOUNDS | | |
| Glucose | 4.50 g/l | 4.50 g/l |
| Hepes | 20 mM | 20 mM |
| Phenol Red | 0.010 g/l | 0.110 g/l |
| Sodium Pyruvate | 0.110 g/l | 0.110 g/l |
| BSA | 0.3% | 0.3% |
| PE | 0.5 μM | 0.5 μM |
| AMINO ACIDS | | |
| L-Arginine/HCl | 0.0840 g/l | 0.0840 g/l |
| L-Cystine | 0.0480 g/l | 0.0480 g/l |
| L-Glutamine | — | 2 mM |
| Glycine | 0.0300 g/l | 0.0300 g/l |
| L-Histidine-HCl-$H_2O$ | 0.0420 g/l | 0.0420 g/l |
| L-Isoleucine | 0.1048 g/l | 0.1048 g/l |
| L-Leucine | 0.1048 g/l | 0.1048 g/l |
| L-Lysine-HCl | 0.1462 g/l | 0.1462 g/l |
| L-Methionine | 0.0300 g/l | 0.0300 g/l |
| L-Phenylalanine | 0.0660 g/l | 0.0660 g/l |
| L-Serine | 0.0420 g/l | 0.0420 g/l |
| L-Threonine | 0.0952 g/l | 0.0952 g/l |
| L-Tryptophan | 0.0160 g/l | 0.0160 g/l |
| L-Tyrosine | 0.0720 g/l | 0.0720 g/l |
| L-Valine | 0.0936 g/l | 0.0936 g/l |
| VITAMINS | | |
| Co-D-Pantothenate | 0.004 g/l | 0.004 g/l |
| Choline Chloride | 0.004 g/l | 0.004 g/l |
| Folic acid | 0.004 g/l | 0.004 g/l |
| Inositol | 0.008 g/l | 0.008 g/l |
| Nicotinamide | 0.004 g/l | 0.004 g/l |
| Pyridoxine-HCl | 0.004 g/l | 0.004 g/l |
| Riboflavin | 0.0004 g/l | 0.0004 g/l |
| Thiamine-HCl | 0.004 g/l | 0.004 g/l |
| Vitamin C | — | 0.030 g/l |
| Retinoic acid | 10 nM | 100 nM |
| Trace elements | — | 10 nM |

TABLE 1-continued

| | Culture media: | |
|---|---|---|
| Constituents | Medium A50 | Medium B50 |
| HORMONES | | |
| Insulin | 0.005 g/l | 0.005 g/l |
| EGF | 1 ng/ml | 1 ng/ml |
| Transferrin | 0.005 g/l | 0.005 g/l |
| T3 | — | 100 nM |
| Dexamethasone | — | 1 nM |
| Hydrocortisone | — | 10 nM |
| Bovine pituitary extract | — | 0.038 g/l |
| ANTI-BACTERIAL | | |
| Fungizone | 0.25 µg/ml | 0.25 µg/ml |
| Penicillin | 2.5 U/ml | 2.5 U/ml |
| Streptomycin | 5 µg/ml | 5 µg/ml |
| Gentamycin | 10 µg/ml | 10 µg/ml |

(PE: mixture of phosphorylethanolamine and ethanolamine)

Comparative Example

Figure 1:
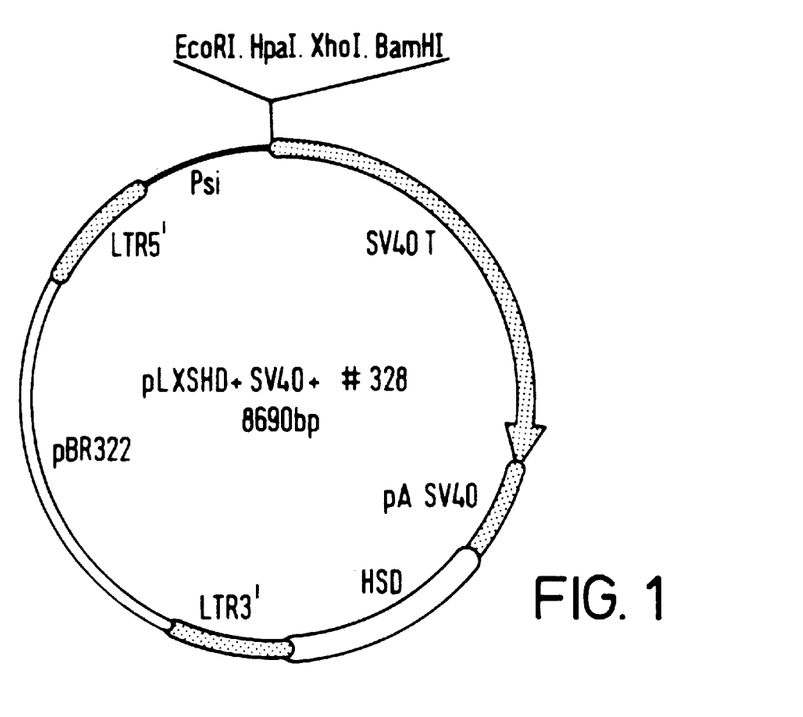
FIG. 1: vector pLXSHD+SV40+ used to immortalize the epithelial cells of the human colon.

The vector pLXSHD+SV40+ described by Stockshlaeder et al. (GeneBank, accession No. M64753; Stockshlaeder et al., Human Gen. Therapy, 2, 33–39), which is represented in FIG. 1, and which comprises the gene encoding the large T antigen, the psi gene, the selectable marker histidinol dehydrogenase (HSD), and the LTR promoter, is used.

The SV40 viruses are prepared according to a modified version of the Lynch and Miller procedure (J. Virol., 65, 3887–3890, 1991). For that, the ecotropic cell lines Psi2 (Mann et al., Cell, 33,153–159, 1983) and the amphotropic cell lines PA317 (ATCC CRL9078) are cultured in the DMEM medium (Dulbecco, USA) comprising 10% foetal calf serum, at 37° C. and under an atmosphere comprising 5% $CO_2$. These lines are conventionally transfected separately using 250 mM $CaCl_2$ and 10 µg of the vector the vector pLXSHD+SV40+, they are subjected to a treatment with trypsin after 48 h of incubation, they are mixed in an equal quantity, and the whole is incubated at 37° C., under an atmosphere comprising 5% $CO_2$. After growing up to 70% confluence, the viruses are harvested in the serum-free medium PC-1 (Ventrex, USA). After filtration (0.45 µm, Micropore), the quantity of virus is determined on NIH 3T3 cells (ATCC CRL 1658).

Primary cells of the colon were obtained following biopsy on a 69-year old woman due to the appearance of a sigmoid diverticulum. The sample is washed in the DMEM culture medium, it is cut into pieces, the epithelial part is separated from the other tissues, the epithelial cells on plates are inoculated into the DMEM medium. The culture plates were preincubated in a 500 ml solution comprising 5 mg of human fibronectin (Sigma), 5 ml of Vitrogen 100 (Collagen Corp. Palo Alto, Calif., USA) 50 ml of a 0.1% BSA solution (Biofluids ) and the remainder of the DMEM medium. The culture medium containing the epithelial cells is changed as many times as necessary in order to optimize a confluent growth.

After having reached a confluence of the order of 90% after 1 week of culture, the cells are conventionally separated by treatments in solutions of trypsin and EDTA. The cells separated are transferred onto culture plates having the coating described above, and in the A50 medium described above.

The cultures are then infected in the presence of 8 µg/ml of polybrene and a high recombinant SV40 virus titre ($10^5$–$10^7$ CFU) comprising the T Antigen (T-Ag) prepared as described above. After 2 h of incubation, the cultures are washed in PBS and the A50 fresh growth medium is added.

The cells unfortunately subsequently exhibit a growth which is so slow that it proves impossible to select a clone having a growth comparable to that of epithelial cells of the human colon.

EXAMPLE 1

The epithelial cells of the human colon are infected as described in the comparative example above, the only difference being that the A50 medium is replaced with the B50 medium described in Table 1 above.

After 2 h of incubation with the virus, the cultures are washed in PBS, the B50 fresh growth medium is added and the cells are cultured by successive passages in fresh B50 medium, being careful at each passage to separate the cells by a treatment in a solution comprising 0.02% trypsin, 1% polyvinyl-pyrolidine and 0.02% ethylene glycol in the HEPES buffer (Biofluids).

By observing the size of the cell colonies which develop on the culture plates, those which develop rapidly are selected. It was thus possible to select 6 human epithelial colon immortalized cell lines, of which one was deposited at the Deutsche Sammlung Von Mikroorganismen und Zellkulturen (DSM), Mascheroder Weg 1b, D-38124 Braunschweig, Germany, on Apr. 16, 1996, where it received the deposit number DSM ACC2258.

1. Analysis of the karyotype of the strain DSM ACC2258.

4 karyotypes of the DSM ACC2258 strain taken at the 40th passage are prepared (method described in the manual "Human cytogenetics, Edts: Rooney DE, Czepulkowski BH, IRL Press, Oxford, 1986", incorporated by reference). The results show that 6 different chromosomes were lost or damaged. The line therefore conserves intact in its genome a chromosome of each pair of chromosomes. The sex of the line is XO/XX. It should be noted that the loss of one set of a chromosome is not a sign of a tumorigenic transformation of the said line.

2. Tumourigenicity of the strain DSM ACC2258

$10^7$ cells of the DSM ACC2258 line, taken at the 46th passages, are injected into mice without immune defence ("nude") according to the procedure described by Stauffer et al. (above). No tumour formation is visible after more than 8 months. The non-tumourigenicity of the lines is not a sign of a non-tumorigenic transformation of the said line. Indeed, by way of example, the NMC456 line described by Stauffer et al. does not induce tumours in nude mice, although it expresses tumour markers characteristic of its tumorigenic transformation.

3. Expression of tumour markers in the DSM ACC2258 line

It is determined according to the procedure described by Stauffer et al. whether the DSM ACC2258 line expresses the following tumour markers: the p-53 mutation, the carcinoembryonic antigen (CEA) and mutation in the adenoma colyposis coli (APC) gene.

The results are negative for all these markers, which indicates a state of non-tumorigenic transformation of the line.

4. Viral contamination of the DSM ACC2258 line

It is determined whether the DSM ACC2258 line is contaminated by the hepatitis C virus (HCV), the hepatitis B virus (HBV) and the AIDS virus (HIV-1).

For the analysis of HBV, DNA is extracted from about $2 \times 10^6$ cells by treating with phenol and chloroform solutions followed by a precipitation in ethanol. DNA samples are then subjected to a PCR amplification using primers specific for the pre-core region of the virus (Lynch et al., J. Virol., 65, 3887–3890). The amplification products are then separated on an agarose gel, and they are visualized under UV in the presence of ethidium bromide. For comparison, a dilution of a serum containing $10–10^5$ HBV (Anawa Biomedical Services 6 Product, USA) is analysed in the same manner, in parallel.

For the analysis of HIV-1, DNA samples described above are subjected to a PCR amplification using primers specific for the GAG region of the virus. The amplification products are then separated on an agarose gel, and they are visualized under UV in the presence of ethidium bromide. For comparison, a dilution of a serum containing $10–10^5$ HIV-1 (Anawa Biomedical Services 6 Product, USA) is analysed in the same manner, in parallel.

For the analysis of HCV, the RNA is extracted from about $2 \times 10^6$ cells by the method of Chomczynski et al. (Anal. Biochem., 162, 156–159, 1987). A reverse transcription is carried out conventionally, and the complementary DNA obtained is subjected to a PCR amplification using primers specific for the non-coding 5' region of the virus. The amplification products are then separated on an agarose gel, and they are visualized under UV in the presence of ethidium bromide. For comparison, a dilution of a serum containing $10–10^5$ HCV (Anawa Biomedical Services 6 Product, USA) is analysed in the same manner, in parallel.

The results are negative for the presence of the 3 viruses.

5. Expression of markers specific for the human epithelial cells 5.a. Cytokeratins: The cells of a culture of the DSM ACC2258 line are attached onto glass plates by a 100% cold methanol solution, and then the plates are washed in a buffer comprising 0.05M Tris pH 8.6, 1.8% NaCl and 0.2% polyethylene glycol 2000 (TNP buffer). The cells are then incubated for 30 min in the presence of mouse antibodies specific for certain cytokeratins (anti-CH peptide 4, 7, 8, 13, 14, 17, 18, 19, 20, Sigma, USA). After 3 washes in the TNP buffer comprising 0.5% BSA, the plates are incubated for 30 min with a goat anti-mouse IgG antibody comprising an immunofluorescent compound (1:300, FITC goat anti-mouse IgG; Biosys). After 3 washes in the preceding buffer, the plates are fixed and they are analysed by fluorescence microscopy. All the cells are positive for the cytokeratins 7, 8 and 17.

5.b. Vimentin: In the same manner as for the analysis of the cytokeratins, the fixed cells described above are subjected to a mouse anti-vimentin antibody (DAKO, USA), and then to the goat anti-mouse IgG antibody mentioned above. By fluorescence microscopy, all the cells are positive for vimentin.

5.c. Connections between the cells (tight junctions): The cells of the DSM ACC2258 line are cultured on a glass plate until they become confluent, they are fixed by treatment with a 2.5% glutaraldehyde solution in a 0.1 M phosphate buffer pH 7.4 for 1 h, at room temperature. After two washes in the same phosphate buffer, the cells are again fixed in a 2% $OsO_4$ solution in the same buffer. The cells are then dehydrated in successive solutions of ethanol at 30, 50, 70, 90 and 100% (Polaron Equipment Ltd., Watford, UK), and then the cells are recovered by a fine gold layer (SEM coating unit E5100, Polaron), The cells are then examined by electron microscopy (Philips 505 SEM). The analysis shows that the cells have intercellular connections which are characteristic of the epithelial cells.

Figure 2:
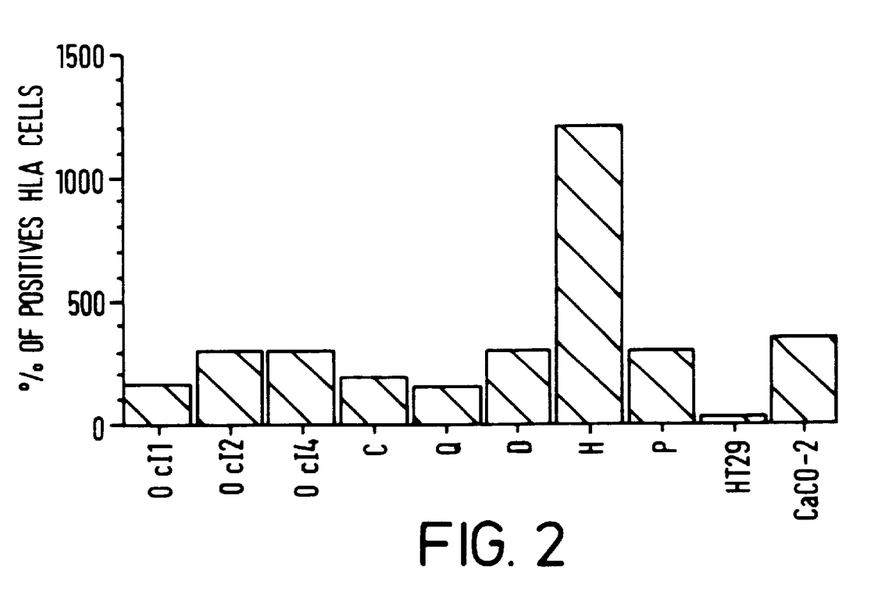
FIG. 2: expression of the intestine alkaline phosphatase activity by different cell lines derived from epithelial cells of the human colon.

5.d. Alkaline phosphatase: The alkaline phosphatase activity of the cells of the DSM ACC2258 line is determined with the aid of the Sigma commercial kit which reproduces the method described by Dahlquist et al. (Analytical Biochemistry, 22, 99–107, 1968). The results presented in FIG. 2 show that the cells of the DSM ACC2258 line (Oc11, Oc12, Oc14) express a phosphatase activity comparable to that of the human colon epithelial cancer cells CaCO-2, but greater than human colon epithelial cancer cells HT-29. The results C, Q, D, H, P relate to other human colon epithelial lines presented in Example 2.

5.e. Cytochrome P450: The expression of cytochromes by the cells of the DSM ACC2258 line is analysed with the aid of the known RT-PCR technique using DNA primers specific for the different cytochromes P450. These primers were conventionally prepared from the DNA sequence of the different cytochromes available on the GeneBank data base (CYP1A1: accession No. X02612; CYP2C: accession No. M61855 or M61858 or M61856 or MM61854; CYP2D6: accession No. M33388; CYP2E1: accession No. J02843; CYP3A5: accession No. J04813; CYP1A2: accession No. Z00036; CYP2A6: accession No. M33318; CYP2B6: accession No. M29874).

For that, the cells are cultured until they become confluent on 35 mm dishes (Costar), the RNA is extracted with the aid of the RNAeasy kit (Qiagen), a reverse transcription is performed (1st Strand cDNA Synthesis Kit for RT-PCR, Boehringer Mannheim), the complementary DNA obtained is subjected to a PCR amplification using DNA primers specific for the different cytochromes P450, the amplification products are then separated on an agarose gel, and they are visualized under UV in the presence of ethidium bromide.

The results show that the cells express cytochromes CYP1A1, CYP2C, CYP2D6, CYP2E1 and CYP3A5. On the other hand, the cells are negative for the cytochromes CYP1A2, CYP2A6 and CYP2B6. The expression of cytochrome CYP3A5 is also confirmed by western-blot analysis of a protein extract of the DSM ACC2258 cells with the aid of an anti-CYP3A5 polyclonal antibody (Oxygene, USA)

5.f. Enzymes involved in the cellular oxidation and the detoxification of electrophiles: The cells of the DSM ACC2258 line are cultured, the RNA is extracted by the Chomczynski et al. method (Anal. Biochem., 162, 156–159, 1987), DNA probes are prepared from the DNA sequences of the Cu/Zn-superoxide dismutase (SOD), glutathione peroxidase (GP), catalase (CA), glutathione-S-transferase (GST) and quinone reductase (QR), which are available on the GeneBank data base (GST: accession No. X08058; GP: accession No. M21304; CA: accession No. M81578; SOD: accession No. 729336; QR: accession No. M81596_600), and then a Northern-blot is performed on the RNA with these probes to confirm the transcription of these enzymes.

The results show that all the cells express a transcription of the genes encoding the SOD, GP, CA, GST and QR activity. The DSM ACC2258 line therefore expresses enzymes involved in the cellular oxidation and the detoxification of electrophiles.

6. Expression of markers specific for the epithelial cells of the human colon 6.a. Surface villosities: As described in point 5.c above, the analysis by electron microscopy of the cells clearly show the presence of short villosities at the pole opposite that which adheres to the support.

6.b. Sucrose isomaltase: Sucrose-isomaltase is specific for the epithelial cells of the human colon. The presence of sucrose-isomaltase can be demonstrated at the level of the messenger RNA by the RT-PCR technique described above in point 5.e, after exposing a confluent culture of DSM ACC2258 cells for 48 h to 1 ng/ml of human recombinant TGF-β (Becton Dickinson). The DNA primers are conventionally prepared from the DNA sequence of the sucrose-isomaltase gene available on the GeneBank data base (accession No. X63597 S41833 S41836).

6.c. Dipeptidylpeptidase IV: DPPIV is specific for the epithelial cells of the human colon. Its presence can be demonstrated at the level of the messenger RNA by the RT-PCR technique described above in point 5.e. The DNA primers are conventionally prepared from the DNA sequence of the DPPIV gene accessible on the GeneBank data base (accession No. U13710-35).

6.d. Class II major histocompatibility complex: The epithelial cells of the colon can express the class II major histocompatibility complex (HLA antigens) in the presence of y-interferon (γ-IFN). For that, the DSM ACC2258 cells are cultured in the B50 medium, in the presence of 100 U/ml of recombinant γ-IFN (Boehringer Mannheim) at 12, 24, 36 and 48 h of culture. The cells are separated by a solution comprising 0.025% trypsin and EDTA (Gibco Life Technologie, USA), and they are incubated in the presence of antibodies specific for the HLA-DR, HLA-DP and HLA-DQ antigens (Becton-Dickinson, USA), and they are separated using a flow cytometer (FACS can, Becton-Dickinson).

Figure 3:
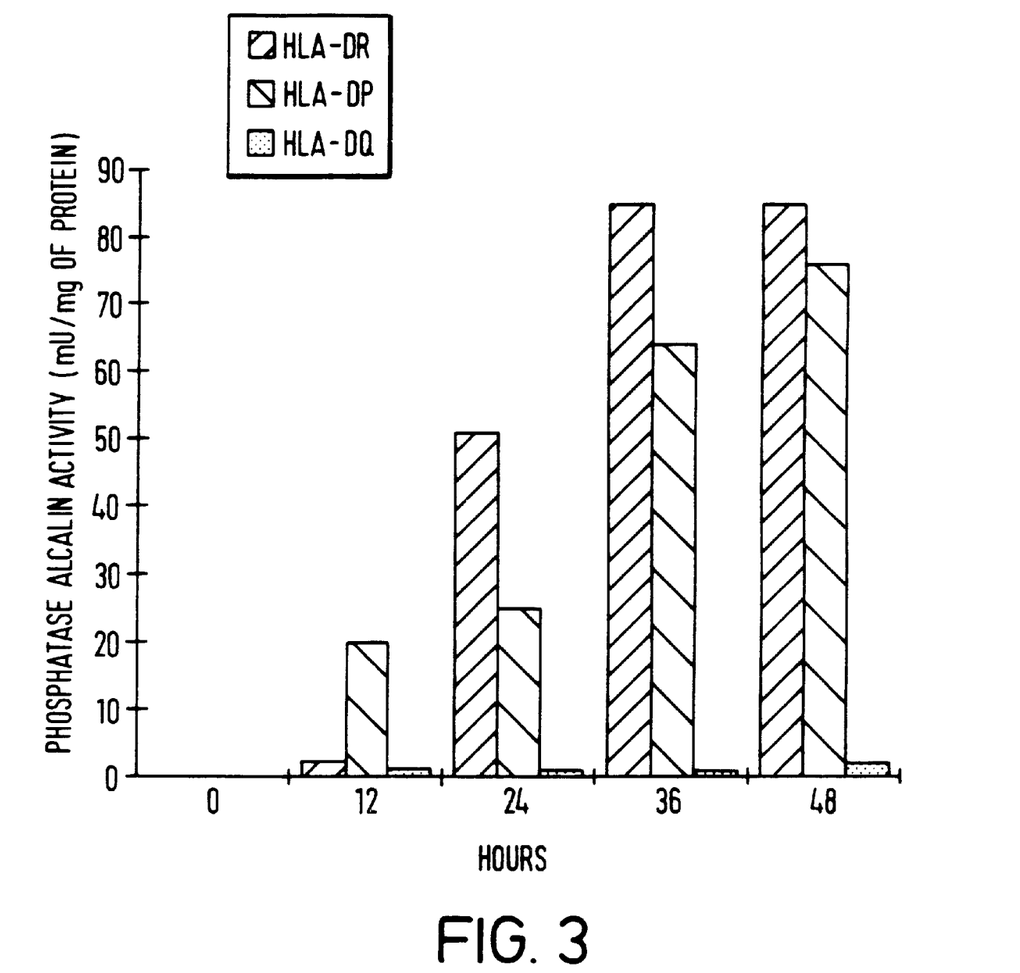
FIG. 3: percentage of immortalized epithelial cells according to the invention which express class II MHC (HLA) antigens in the presence of gamma-interferon, as a function of time.

The results presented in FIG. 3 show an expression of the HLA-DP antigen from 12 h of culture, with increasing concentrations at 24 and 48 h. The expression of HLA-DR is observed after 24 h of culture with maximum concentrations at 36 and 48 h. On the other hand, the HLA-DQ antigen is not induced, which confirms the observations made on the primary epithelial cells of the colon (Mayer et al.).

7. Adhesion to microorganisms 7.a. Adhesion to the strain of bacterium CNCM-I-1225: The human intestine is colonized by numerous non-pathogenic bacteria, among which there are the lactobacilli and the bifido bacteria, some of which are capable of adhering to the villosities of the intestinal mucous membrane. The *Lactobacillus johnsonii* strain CNCM-I-1225, known to strongly adhere to the epithelial cells of the intestinal tract (EP577904; Bernet et al.), is thus cultured for 12 h in an MRS medium (Man, Rogosa and Sharpe, Biokar) comprising 100 μC of $^3$H-adenine, in the absence of oxygen.

The DSM ACC2258 cells are cultured for 2 weeks until they become confluent, and then they are incubated for 1 h at 37° C. with the 12-h MRS medium described above, or a fresh MRS medium or a phosphate buffer pH 6.5 comprising 4×10$^8$ cells per ml derived from the 12-h MRS culture described above. The DSM ACC2258 cells are washed 3 times with PBS, they are lysed with a 1 M NaOH solution, then the radioactive intensity released by the cells is measured with the aid of a scintillation counter.

For comparison, the strain CaCO-2 is cultured in the same manner as described above, it is incubated with the strain CNCM I-1225 and the radioactive intensity released by the cells is measured.

The results presented in Table 2 below show that the DSM ACC2258 cells are capable of adhering the CNCM I-1225 bacteria, as well as the CaCO-2 cells. It can also be noted that the culture of the 12-h LA-1 strain manifestly contains factors which promote the adhesion of the bacteria. Indeed, the fresh MRS medium to which bacteria were added exhibits a lower adhesion level. Furthermore, it can be observed that a pH of 6.5, which is similar to that found in the intestinal tract in vivo, also promotes the adhesion of the bacteria, when a comparison is made with the adhesion level obtained with the fresh MRS medium having a pH of the order of 5.

TABLE 2

| Cell line | Incubation conditions | % $^3$H-adenine |
|---|---|---|
| DSM ACC2258 | 12-h MRS | 30.2 |
| | Fresh MRS | 11.8 |
| | Buffer pH 6.5 | 13.03 |
| CaCo-2 | 12-h MRS | 34.8 |
| | Fresh MRS | 6.1 |
| | Buffer pH 6.5 | 8.3 |

The capacity of the DSM ACC2258 line has to retain the bacteria CNCM I-1225 is also measured according to the method described by Bernet et al. (Gut, 35, 483–489, 1994). In short, the number of bacteria which adhere to 100 colon cells is determined visually. For that, a 12-h MRS culture medium, or a fresh MRS medium comprising 4×10$^8$ cells per ml derived from this 12-h MRS culture, is used. Furthermore, the analysis is carried out on three preparations, and 20 micrographs taken at random in each preparation are used.

For comparison, the capacity of the CaCO-2 line has to retain the bacteria CNCM I-1225 is also measured in the same manner.

The results presented in the Table below shows that the line is capable of retaining a significant number of bacteria. It can also be noted that the culture of the 12-h LA-1 strain manifestly contains factors which promote the adhesion of the bacteria. Indeed, the fresh MRS medium to which bacteria were added does not make it possible to obtain such a high adhesion level.

TABLE 3

| Cell line | Incubation conditions | No./100 cells | Standart deviation |
|---|---|---|---|
| DSM ACC2258 | 12-h MRS | 118 | 7 |
| | Fresh MRS | 13 | 4 |
| CaCo-2 | 12-h MRS | 124 | 13 |
| | Fresh MRS | 9 | 4 |

7.b adhesion to *Clostridium difficile* and/or adherent bifidobacteria: The capacity of the DSM ACC2258 line has to retain the bacteria *Clostridium difficile* and adherent bifidobacteria described in Applied Env. Microb., 59, 4121–4128, 1993 and in EP577904 (Nestlé) has been also analysed. The results shows that the line is also capable of retaining a significant number of each bacteria.

8. Cytokines expression: The expression of cytokines by the cells of the DSM ACC2258 line, in presence or absence of an infammation agent, is analysed with the aid of the known RT-PCR technique using DNA primers specific for different cytokines. These primers were conventionally prepared from the DNA sequence of the different cytokines available on the GeneBank data base (accession number: TNFα: X02910; IL-1β: M15840; IL-6: M14584; IL-8: M28130; IL-ra: M97748). Induction of inflammation was carried out by incubation of the line with 1 mM histamine or 20 ng/ml TPA during 24 h.

For comparison, same analysis were carried out with a normal colon tissue, HT-29 and CaCO-2 tumorigenic cell lines. The results are presented in Table 4 below.

TABLE 4

| mRNA | colon tissue non-induced | DSM ACC2258 non-induced/induced | | HT-29 non-induced/induced | | CaCO-2 non-induced/induced | |
|---|---|---|---|---|---|---|---|
| IL-1β | + | + | ++ | − | ++ | − | + |
| IL-ra | − | − | + | + | ++ | − | + |
| TNFα | − | + | ++ | + | ++ | + | ++ |
| IL-6 | + | + | ++ | + | ++ | + | ++ |
| IL-8 | − | + | ++ | + | ++ | + | ++ |

EXAMPLE 2

The other immortalized human epithelial colon cell lines developed in Example 1 exhibit characteristics similar to those described above for the DSM ACC2258 strain. By way of example, the alkaline phosphatase activity of 5 other lines called C, Q, D, H, P are presented in FIG. 2.

What is claimed is:

1. A cell of an immortalized adult human colon epithelial cell line, which cell does not express a mutant-p53 gene, adenomatous polyposis coli gene or carcinoma embryonic antigen;
    expresses metabolic markers specific for non-immortalized human epithelial cells;
    expresses metabolic differentiation markers specific for non-immortalized human colon epithelial cells;
    adheres in vitro to the strain of lactic acid bacterium CNCM 1-1225; and contains a viral gene;
    wherein the cell line is capable of Undergoing at least 60 passages in culture due to expression of the viral gene in the cells of the cell line.

2. The cell of claim 1, which expresses at least two metabolic markers specific for non-immortalized human epithelial cells, wherein each of the two metabolic markers is selected from the group consisting of cytokeratins, connections between the cells, alkaline phosphatase, cytochrome glutathione-S-transferase, quinone reductase, Cu/Zn-superoxide dismutase, glutathione peroxidase and catalase.

3. The cell of claim 1, which expresses at least two metabolic differentiation markers for non-immortalized human colon epithelial cells, wherein each of the two metabolic differentiation markers is selected from the group consisting of surface villosities, sucrose isomaltase, class II major histocompatibility complex which is specific to human colon epithelial cells, and dipeptidylpeptidase IV.

4. The cell of claim 3, which expresses HLA-DR and HLA-DP antigens of the class II major histocompatibility complex, and no HLA-DQ antigen of the complex, in the presence of human gamma-interferon.

5. The cell of claim 1, which adheres in vitro lactic acid bacterium CNCM I-1225 at a level of at least 80 bacteria per 100 cells of the cell line.

6. A cell of the immortalized cell line which has the deposit number DSM ACC2258.

7. A method for producing immortalized adult human colon epithelial cells which comprises:
    culturing primary epithelial cells derived from the adult human colon; infecting cultured primary epithelial cells with a recombinant virus; and
    culturing infected epithelial cells in a serum-free culture medium to obtain the immortalized adult human colon epithelial cells, wherein the serum free culture medium comprises trace elements, vitamin C, retinoic acid, triiodothyronine, dexamethasone, hydrocortisone, bovine pituitary gland extract, insulin, EGF and transferrin and calcium present at a concentration of less than 80 μM.

8. The method according to claim 7, in which the recombinant virus is an SV40 T-Ag recombinant virus containing an inactivated replication orgin of an MuLV retrovirus.

9. A cell line having the cell of any one of claims 1–6.

10. A cell which is produced by the method of claim 7 or 8.

11. The method according to claim 7, wherein the serum-free culture medium comprises 1–100 nM trace elements, 10–1,000 riM retinoic acid, 10–1,000 nM triiodothyronine, 0.1–50 nM dexamethasone, 1–100 nM hydrocortisone, 1–100 μg/ml of vitamin C, 1–100 μg/ml of bovine pituitary gland extract, 0.1–50 μg/ml of insulin, 0.1–50 ng/ml of EGF and 0.1–100 μg/ml of transferrin.

12. The method according to claim 7, wherein the serum-free culture medium additionally comprises inorganic salts comprising at least one salt selected from the group consisting of sodium chloride, potassium bicarbonate, ferric nitrite, ammonium metevanadate, ammonium molybdate, cupric sulphate, magnesium chloride, manganese chloride, nickel sulphate, sodium acetate, sodium pyruvate, sodium selenite, sodium silicate, tin chloride, and zinc sulphate.

13. The method according to claim 7, wherein the serum-free culture medium additionally comprises at least one vitamin selected from the group consisting of calcium D-pantothenate, choline chloride, folic acid, inositol, nicotinamide, pyridoxine, riboflavin, thiamine, biotin and cyanocobalamine.

14. The method according to claim 7, wherein the serum-free culture medium comprises 6.4 g/l NaCl, 0,4 g/l KCl, 0.2 g/l MgSO$_4$-7H$_2$O, less than 0.0088 g/l CaCl$_2$, 0.13 g/l NaH$_2$PO$_4$-H$_2$O, 3.7 g/l NaHCO$_3$, 0.0001 g/l Fe(NO$_3$)$_2$ 9H$_2$O, 4.5 g/l glucose, 20 mM Hepes, 0.01 g/l phenol red, 0.11 g/l sodium pyruvate, 0.3% bovine serum albumin, 0.5 [@] μM PE, 0.084 g/l L-arginine-HCl, 0.048 g/l L-cystine, 2 mM L-glutamine, 0.03 g/l glycine, 0.042 g/l L-histidine-HCl-H$_2$O, 0.1048 g/l L-isoleucine, 0.1048 g/l L-leucine, 0.1462 g/l L-lysine-HCl, 0.03 g/l L-methionine, 0.066 g/l L-phenylalanine, 0.042 g/l L-serine, 0.0952 g/l L-threonine, 0.0160 g/l L-tryptophan, 0.072 g/l L-tyrosine, 0.0936 g/l L-valine, 0.004 g/l Ca-D-pantothenate, 0.004 g/l choline chloride, 0.004 g/l folic acid, 0.008 g/l inositol, 0.004 g/l nicotinamide, 0.004 g/l pyridoxine-HCl, 0.0004 g/l riboflavin, 0.004 g/l thiamine-HCl, 0.03 g/l vitamin C, 100 nM retinoic acid, 10 nM trace elements, 0.005 g/l insulin, 1 ng/ml EGF, 0.005 g/l transferrin, 100 nM triiodothyronine, 1 nM dexamethasone, 10 nM hydrocortisone, 0.038 g/l bovine pituitary extract, 0.25 [@] μg/ml fimgizone, 2.5 U/ml penicillin, 5 [@] μg/ml streptomycin, and 10 [@] μg/ml gentamycin, wherein PE is a mixture of ethanolamine and phosphorylethanolamine.

* * * * *

UNITED STATES PATENT AND TRADEMARK OFFICE
CERTIFICATE OF CORRECTION

PATENT NO. : 6,194,203 B1
DATED : February 27, 2001
INVENTOR(S) : Stephanie Blum Page 1 of 1

It is certified that error appears in the above-identified patent and that said Letters Patent is hereby corrected as shown below:

Claim 1, line 30, replace "1-1225" with --I-1225--.

Claim 1, line 31, replace "Undergoing" with --undergoing--.

Claim 2, line 39, after "chrome" insert --P450,--.

Claim 8, line 17, replace "orgin" with --origin--.

Claim 11, line 23, replace "riM" with --nM--.

Claim 12, line 31, after "potassium" insert --chloride, potassium sulphate, calcium chloride, dibasic sodium phosphate, sodium--.

Claim 14, line 43, replace "0,4" with --0.4--.

Claim 14, line 45-46, replace "Fe(NO$_3$)$_2$ 9H$_2$O" with --Fe(NO$_3$)$_2$-9H$_2$O--.

Claim 14, line 48, "[@]".

Claim 14, line 61, delete "[@]" and replace "fimgizone" with --fungizone--.

Claim 14, line 62, delete "[@]" in both instances.

Signed and Sealed this

Third Day of July, 2001

Attest:

NICHOLAS P. GODICI
*Attesting Officer*  *Acting Director of the United States Patent and Trademark Office*